United States Patent [19]

Wu

[11] Patent Number: 4,495,198

[45] Date of Patent: Jan. 22, 1985

[54] ANTIHYPERTENSIVE CHROMONOXYPROPANOLAMINES

[75] Inventor: Edwin S. Wu, Rochester, N.Y.

[73] Assignee: Pennwalt Corporation, Philadelphia, Pa.

[21] Appl. No.: 441,890

[22] Filed: Nov. 15, 1982

Related U.S. Application Data

[63] Continuation-in-part of Ser. No. 259,403, May 1, 1981, abandoned, and a continuation-in-part of Ser. No. 422,929, Sep. 24, 1982, abandoned.

[51] Int. Cl.$^3$ .............................................. A61K 31/35
[52] U.S. Cl. ................................... 514/456; 549/401; 549/403
[58] Field of Search ................. 549/401, 403; 424/283

[56] References Cited

U.S. PATENT DOCUMENTS 4,391,821  7/1983  Korbonits et al. .................. 549/401

OTHER PUBLICATIONS

Wang et al., Chem. Abstr., 94, 65430a (1981)–Abstract of Yao Hsueh Hsueh Pao, -15, 253 (1980).
Chinoin et al., Chem. Abstr., 96, 199528p (1982)–Abstract of Belg. Be 889,665 (11/16/81).
Korbonits et al., Chem. Abstr., 97, 198113h (1982)–Abstract of Brit. UK Pat. Appl. GB 2,089,338 (6/23/82).

Primary Examiner—Nicky Chan

[57] ABSTRACT

Chromone derivatives such as 6 or 7-(3-amino-2-hydroxypropoxy)-2-phenylchromones, -3-phenylchromones or -2,3-diphenylchromones which are useful as antihypertensive agents.

10 Claims, No Drawings

ANTIHYPERTENSIVE CHROMONOXYPROPANOLAMINES

This is a continuation-in-part of U.S. Ser. No. 259,403 filed May 1, 1981, now abandoned and U.S. Ser. No. 422,929 filed Sept. 24, 1982, now abandoned.

BACKGROUND OF THE INVENTION

This invention relates to chromone derivatives substituted by 3-amino-2-hydroxypropoxy side chains, medicinal preparations containing the same, and the utilization of such preparations as antihypertensive agents in animals.

Compounds related to propranolol, a potent beta-blocker, constitute a large class of compounds which have profound effects on the cardiovascular system and have found utility as antihypertensive, antidysrhythmic and antianginal drugs. However, the beta-blocking properties of these compounds are often undesirable, especially in patients with coronary insufficiencies and bronchial diseases. A compound devoid of beta-blocking effect but retaining antihypertensive effect on the blood pressure of warm-blooded animals has long been sought.

Several patents disclose various compounds which either have beta-blocking properties or do not have antihypertensive effects. U.S. Pat. No. 3,891,651 discloses compounds which are amides and, it is thought, the nitrogen of the amide which is contained in the isoquinoline fragment is likely to be responsible for any activity in that compound. U.S. Pat. No. 3,816,470 discloses various salts of secondary amines with chromone-2-carboxylic acids. U.S. Pat. No. 3,812,156 discloses a method of preparing ethyl flavone-7-oxyacetate. U.S. Pat. No. 3,352,754 discloses simple 7-hydroxy or 7-alkoxy isoflavones which are not amines and which are used for various inflammatory disorders. U.S. Pat. No. 3,219,531 discloses 5,7-dioxyacetic acid flavone compounds, but no amine functions are present. U.S. Pat. No. 3,046,275 discloses 7-dialkylaminoalkoxy derivatives but does not contain any of the hydroxyl groups of the side chain which is central for activity. Various monodialkyl aminoethyl ethers of quercetin are disclosed in U.S. Pat. No. 2,861,992, but do not contain 3-amino-2-hydroxypropoxy side chains. Also not containing that side chain are the compounds disclosed in U.S. Pat. No. 2,897,211.

P. Da Re et al, *J. Med. Chem.*, Vol. 15, 868–869 (1972), describe the testing of chromones as in formula (1), but where $R_3$ is methyl, for beta-adrenergic blocking activity. Da Re et al. found that all the compounds were devoid of beta-blocking activity, suggesting that chromones would not be expected to have antihypertensive properties. Additionally, ethanolamine analogues of the Da Re et al. materials are disclosed in Vol. 15 pages 198–199 of the *J. Med. Chem.* (1972). The analogues are beta-blockers, typical of the pronethalol type which owe their activity to the 2-isopropylaminoethanol side chain. Typical 3-amino-2-hydroxypropoxy side chain furochromone compounds are disclosed in papers presented in *Drugs of the Future*, Vol. III, No. 8 (1978), pages 569–571; *Drugs of the Future*, Vol. III, No. 11, (1978), pages 816–818; and *Therapie*, (1977), Vol. 32, pages 111–120. None of these references, of course, even suggest that antihypertensive activity may be possible with or without beta-blocking. None of these references discloses the process of this invention.

Wang et al., *Acta Pharmaceutical Sinica*, Vol. 15, pages 253–256 (1980), while disclosing compounds within Formula 1 below, fails to teach hypertensive efficacy for analogues with the amine side chain substituent in the 6 or 7 position.

SUMMARY OF THE INVENTION

It has now been found that a marked reduction in the blood pressure of warm-blooded animals can be achieved, without beta-blocking effects in the beta-adrenergic nervous system, by administering to the animal, in an amount effective to reduce hypertension, a chromone of the formula:

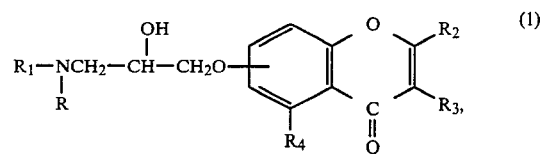

or a pharmaceutically acceptable acid addition or quaternary ammonium salt thereof where the side chain can be in the 6 or 7 position of the chromone nucleus and where R is hydrogen or methyl, $R_1$ is hydrogen, primary or secondary alkyl of 1 to 6 and preferably 1 to 4 carbons, or cycloalkyl of 3 to 6 carbons, or lower alkenyl, $R_2$ is hydrogen, lower alkyl, $CF_3$, phenyl, ortho halophenyl or para halophenyl; and $R_3$ is hydrogen or phenyl, or benzyl and $R_4$ is H or OH; with the proviso that at least one of $R_2$ or $R_3$ is phenyl or substituted phenyl.

It has further been discovered that chromones of formula (1) above where the side chain is in the 6 or 7 position of the chromone nucleus, $R_1$ is i-propyl, n-propyl or cyclopropyl, $R_2$ is phenyl, $R_3$ is phenyl or hydrogen (with the proviso that $R_1$ is cyclopropyl or n-propyl when $R_3$ is hydrogen) and $R_4$ is H or OH and R is hydrogen have unexpectedly superior antihypertensive properties, especially in terms of being able to achieve long-term activity (e.g., 24 hours) at relatively low dosages.

The compounds are usually mixed with a pharmaceutical carrier so that the composition for commercial use contains 0.5 to 20% by weight of the compound.

The compositions are normally adapted for peroral or parenteral use, but may be used in other forms such as suppositories. The peroral compositions are preferably in the form of tablets, capsules or suspensions, while the parenteral composition is preferably an injectable solution or suspension.

Examples of suitable inert pharmaceutical carriers are celluloses (particularly microcrystalline celluloses), sugar syrups, potato starch, talcum, polyethylene glycols and lactose.

Examples of suitable acids fo forming the acid addition salts are maleic acid, hydrochloric acid, sulfuric acid, phosphoric acid, methanesulfonic acid, tartaric acid, citric acid, and the cation exchange resins such as the carboxylic acid, phosphonic acid and sulfonic acid resins.

For sustained release, a coated complex of the compound absorbed onto an ion exchange resin may be employed in accordance with the teaching of British Pat. No. 1,544,761.

The usual peroral dosage of the compound is 0.1 to 150 mg. per day (preferably 0.1 to 50 mg.) while the parenteral dosage is normally 0.1 to 40 mg. per day (preferably 0.1 to 10 mg.).

The capsules, tablets, syrups and suspensions of the compounds are prepared by conventional procedures.

It should be noted that the compounds of this invention are antihypertensive agents, not hypotensive agents, i.e., they reduce the blood pressure to normal but not below normal.

DESCRIPTION OF THE INVENTION

The compounds of formula (1) above can be prepared by reacting epichlorohydrin or epibromohydrin with a compound of the formula

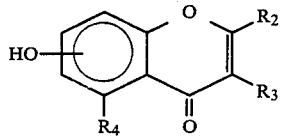

wherein $R_2$, $R_3$ and $R_4$ are the same as defined above and the hydroxyl group is substituted on 6 or the 7 position, in the presence of a solvent and a base to give a product of formula (2) where the hydrogen of the hydroxyl is substituted by

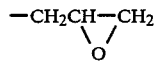

This epoxide is allowed to react with ammonia or an amine in an alcoholic solvent at elevated temperature to afford a product of formula (1). When R or $R_1$ is benzyl, it can be removed by catalytic hydrogenation to give the secondary amine.

The following general procedures are used in the examples as follows:

A. For Epoxides—Epichlorohydrin or epibromohydrin (greater than 2 equivalents) is added in the presence or absence of nitrogen to a stirred solution or suspension of the hydroxy chromone derivative in solvents, such as acetone, aqueous ethanol, 50% aqueous dimethylsulfoxide (DMSO) or water, containing a suitable base, such as potassium carbonate or sodium hydroxide, with or without sodium iodide. The reaction is allowed to proceed either at room temperature or elevated temperature and monitored by thin layer chromatography (tlc). The product, formed as solid, is then collected and washed with water. The mother liquor is diluted with water and extracted with chloroform (CHCl$_3$) to give more product. Where the product is soluble in solvents, the reaction mixture is filtered off and the solids washed with the solvent. The filtrate is evaporated to give a solid which is washed with water to get rid of remaining traces of the base. Yield is in the 60 to 80% range. This material is usually used directly for further reaction without purification.

B. For Epoxide Ring-Opening With Amine and the Amine Salt Formation—A white suspension of the chromone epoxide, amine, such as low (large excess) and high (10% excess) boiling point amines, and alcoholic solvent, methanol (A.R.) ethanol (abs.) or isopropanol, is heated at elevated temperatures until the starting material is gone (as followed by tlc.). Since the reaction product is usually soluble in the alcohol, the precipitate is filtered off and the filtrate is evaporated to give a viscous liquid which, upon addition of anhydrous ether or alcohol, crystallizes out. When the product is insoluble in alcohol at the end of the reaction, it is collected. Purification of the amine derivative is performed via acid-base work-up, column chromatography or recrystallization. The amine obtained is either suspended or dissolved in an alcohol, such as MeOH or abs. ethanol (EtOH) or isopropanol, and then acidified with alcoholic solution saturated with hydrogen chloride or another suitable acid. The salt formed is precipitated out by addition of anhydrous either. The salt is then recrystallized from suitable solvents.

EXAMPLE 1

Preparation of 7-(2-hydroxy-3-isopropylaminopropoxy)-2,3-diphenylchromone hydrochloride 7-(2,3-Epoxypropoxy)-2,3-diphenylchromone To a solution of 50% aqueous DMSO (280 ml) containing sodium hydroxide (5.60 g, 140 mmol) was added 7-hydroxy-2,3-diphenylchromone (44.01 g, 140 mmol) and the resultant mixture was stirred until most of the solid went into the solution. Epichlorohydrin was then introduced into the suspension. The solution was stirred at room temperature (RT) for 2.5 days and solid formed during the reaction was collected from time to time (about twice a day). The white solid (total=47.58 g) was recrystallized from isopropyl alcohol several times to afford 28.15 g of relatively pure white prisms, m.p. 143°–145°; yield 54%. The mother liquor was concentrated to produce more crystals.

7-(2-Hydroxy-3-isopropylaminopropoxy)-2,3-diphenylchromone hydrochloride

A white suspension of relatively pure 7-(2,3-epoxypropoxy)-2,3-diphenylchromone (27.78 g, 75 mmol), isopropylamine (18.8 ml), and methanol (A.R., 150 ml) was heated under nitrogen at 55° C. until complete disappearance of the starting epoxide. The white precipitate (1.09 g) in the cooled reaction mixture was filtered off, and the filtrate was evaporated to a golden syrup. Anhydrous ether was added, and white crystals (28.07 g) were obtained. It was column-chromatographed over silica gel. This purification yielded 24.05 g of white crystals, m.p. 152°–154° (75%).

The amine thus obtained was dissolved in 100 ml of MeOH A.R. and treated with saturated solution of hydrogen chloride in ethanol until the solution was pH=1. The hydrochloride salt was precipitated out by addition of anhydrous ether. A white solid was collected and recrystallized from MeOH-ether (also decolorized with a small amount of activated charcoal) to produce 21.6 g (83% yield) of pure white crystals, m.p. 164°–166°.

Anal. Calc'd. for $C_{27}H_{28}ClNO_4.H_2O$: C, 67.00; H, 6.25; Cl, 7.32; N, 2.89. Found: C, 67.10; H, 5.95; Cl, 7.19; N, 2.65.

EXAMPLE 2

Preparation of 7-(2-hydroxy-3-isopropylaminopropoxy) flavone hydrochloride 7-(2,3-Expoxypropoxy)flavone Epichlorohydrin (231 g, 195.6 ml, 2.5 mol) was slowly added to a stirred yellow solution of 7-hydroxyflavone (119.0 g, 0.5 mol) in 50% aq EtOH (500 ml) containing NaOH (20.0 g, 0.5 mol) and left to stand at RT. It was left overnight and the white solid, 89.9 g, m.p. 254°–4° (with some solid melting around 120°), was collected and washed with water. The original filtrate of the reaction mixture before water washing was stirred at RT overnight, yielding 73.6 g white solid after filtration and washing with water (at that time, tlc, 2% methanol in chloroform, indicated that only a small amount of the starting flavone was left).

The first crop of the solid was suspended in chloroform (ca 250 ml), stirred for 30 min., and filtered. Evaporation of the chloroform solution afforded the desired epoxide as white crystals (21.12 g) m.p. 121°–124°. Similarly, the second crop of the white solid gave 49.97 g of the epoxide m.p. 119°–121°.

The water washings from the first and second crops were combined and extracted with chloroform. The chloroform extracts were combined and evaporated to yield a white solid, which was washed with water to give 3.11 g, m.p. 114°–115°.

Water was added to the mother liquor from the second crop, and solid was collected. The solid was added to the filtrate, and it was extracted with chloroform twice. The extracts were evaporated to leave a reddish-gold oil which crystallized upon being seeded. The sticky solid was collected and washed with a small amount of anhydrous ether to produce 12.53 g of white crystals, m.p. 120°–125°. Total yield, 86.7 g, is 59%.

It can also be prepared in 68% yield by refluxing under nitrogen 7-hydroxyflavone, epichlorohydrin or epibromohydrin (2 eq), anhydrous potassium carbonate (3 eq), and NaI (1.5 eq) in acetone for about 2 days.

7-(2-Hydroxy-3-isopropylaminopropoxy)flavone hydrochloride

A suspension of 7-(2,3-epoxypropoxy)flavone 19.0 g, 0.065 mol) and isopropylamine (23.05 g, 33.2 ml, 0.39 mol) in methanol (AR, 250 ml) was stirred under nitrogen at RT. After 1.5 days' stirring, the reaction was not completed yet, as evidenced by tlc. It was then heated at 60° for 12 hrs. (to drive the reaction to completion). The solvent and excess of isopropylamine were removed under reduced pressure, thus leaving yellow crystals which, upon washing with anhydrous ether, gave a white solid (14.64 g), m.p. 140°–142°.

The ether washing was evaporated and a yellow sticky solid obtained. It was washed with a small amount of ether, but it remained sticky. Therefore, it was dissolved in a small amount of MeOH (AR) and treated with HCl-saturated EtOH until acidic. The solvents were removed, and the residue was dissolved in water (10 ml) and aq 10% HCl, extracted with chloroform (30 ml×2). The aqueous layer was basified with conc. ammonia and extracted with chloroform (30 ml×4). Chloroform extracts were washed with water and saturated NaCl, and dried (MgSo₄), thus affording 1.0 g of light brown crystals, m.p. 140°–142°. Combined yield, 15.64 g, was 68%.

The free base (14.64 g) in MeOH (AR, 150 ml; a suspension) was treated wiht HCl-saturated ethanol (abs 2B) dropwise. It became a solution when the mixture was acidic, and then pale yellow crystals precipitated out. MeOH was added to make it to 400 ml and heated to bring it to a solution. It was concentrated to 250 ml, and anhydrous ether (800 ml) was added and cooled to give pale yellow prisms (15.92 g, 98.6% yield), m.p. 231°–233°. The yellow color was gone upon drying at 80° under vacuum.

Anal. Calc'd. for $C_{21}H_{24}ClNO_4$: C, 64.69; H, 6.20; Cl, 9.09; N, 3.59; O, 16.41. Found: C, 64.68; H, 6.20; Cl, 9.02; N, 3.56; O, 16.52.

EXAMPLE 3

Preparation of 7-(2-hydroxy-3-isopropylaminopropoxy)-3-phenylchromone hydrochloride 7-(2,3-Epoxypropoxy)-3-phenylchromone 7-Hydroxy-3-phenylchromone and epichlorohydrin were reacted according to general procedure A, and the product obtained was white prisms, m.p. 151°–152° (83% crude yield) from isopropyl alcohol.

7-(2-Hydroxy-3-isopropylaminopropoxy)-3-phenylchromone hydrochloride 7-(2,3-Epoxypropoxy)-3-phenylchromone and isopropylamine were reacted according to Method B to give the product as the hydrochloride in 62% yield, mp. 148°–150° (EtAC-EtOH-Ether). Its corresponding free base, m.p. 128°–130°.

Anal. Calc'd. for $C_{21}H_{24}ClNO_4$: C, 64.69; Cl, 9.09, H, 6.20; N, 3.59. Found: C, 64.63; H, 6.30; Cl, 9.65; N, 3.56.

EXAMPLE 4

Preparation of 7-(3-n-propylamino-2-hydroxypropoxy) flavone hydrochloride

Using Method B, the reaction of 7-(2,3-epoxypropoxy)-flavone and n-propylamine afforded the hydrochloride in 48% yield, m.p. 234°–235° (methanol). Its corresponding free base had a m.p. 140°–145°.

Anal. Calc'd. for $CH_{21}H_{24}ClNO_4$: C, 64.69; H, 6.20; Cl, 9.09; N, 3.59; O, 16.41. Found: C, 64.60; H, 6.37; Cl, 8.44; N, 3.48; O, 16.57

EXAMPLE 5

Preparation of 2'-chloro-7-(2-hydroxy-3 isopropylaminopropoxy) flavone

2'-Chloro-7-(2,3-epoxypropoxy)-flavone

The epoxypropoxy ether was prepared in quantitative yield (crude) from 2'-chloro-7-hydroxyflavone according to Method A.

2'-Chloro-7-(2-hydroxy-3-isopropylaminopropoxy) flavone hydrochloride

The amine was prepared from the epoxide and isopropylamine according to Method B. The yield of recrystallized product (from toluene) was 56%, melting at 114°–116°.

Anal. Calc'd. for $C_{21}H_{22}ClNO_4$: C, 65.03; H, 5.71: Cl, 9.14; N, 3.61; O, 16.41. Found: C, 65.22, H, 6.00; Cl, 9.19; N, 3.56; O, 15.55.

EXAMPLE 6

Preparation of 6-(2-Hydroxy-3-isopropylaminopropoxy) flavone hydrochloride 6-(2,3-Epoxypropoxy)flavone This epoxypropyl ether was obtained in 65% yield from 6-hydroxyflavone according to Method A.

6-(2-Hydroxy-3-isopropylaminopropoxy) flavone hydrochloride

The reaction of the above epoxide with isopropylamine according to Method B yielded (after recrystallization from n-butanol) 49% product, melting at 209°–211°.

Anal. Calc'd. for $C_{21}H_{24}ClNO_4$: C, 64.69; H, 6.20; Cl, 9.09; N, 3.59; O, 16.41. Found: C, 64.59; H, 6.61; Cl, 9.64; N, 3.40; O, 16.02.

EXAMPLE 7

Preparation of 4′-chloro-7-(2-hydroxy-3-isopropylaminopropoxy) flavone hydrochloride 4′-Chloro-7-(2,3-epoxypropoxy)flavone The epoxypropyl ether was prepared in quantiative yield (crude) from 4′-chloro-7-hydroxyflavone according to Method A.

4′-Chloro-7-(2-hydroxy-3-isopropylaminopropoxy) flavone hydrochloride

The amine hydrochloride was prepared from the above epoxide and isopropylamine using Method B. The yield of recrystallized product from dimethylformamide (DMF) was 63%, m.p. 258°–259°.

Anal. Calc'd. for $C_{21}H_{23}Cl_2NO_4$: C, 59.44; H, 5.46; Cl, 16.71; N, 3.30; O, 15.08. Found: C, 59.35; H, 5.60; Cl, 16.96; N, 3.44; O, 15.21.

EXAMPLE 8

Preparation of 7-(3-n-propylamino-2-hydroxypropoxy)-2,3-diphenyl-chromone hydrochloride The free base was prepared according to Method B from n-propylamine and 7-(2,3-epoxypropoxy)-2,3-diphenyl-chromone in 65% yield as white prisms, m.p. 140°–142°. (iPrOH).

The hydrochloride salt was obtained in 95% yield as white prisms, m.p. 134°–136° (iPrOH).

EXAMPLE 9

Preparation of 7-(3-cyclopropylamino-2-hydroxypropoxy)flavone hydrochloride

Using Method B, the amine was prepared from cyclopropylamine and 7-(2,3-epoxypropoxy) flavone and purified by column chromatography, yield 26%. Treatment of the free base with HCl/EtOH solution gave the hydrochloride salt in 95% yield, m.p. 214° (MeOH-ether).

Anal. Calc'd. for $C_{21}H_{22}ClNO_4$: C, 65.03; H, 5.71; Cl, 9.14; N, 3.61; O, 16.49. Found: C, 64.82; H, 5.81; Cl, 9.27; N, 3.65; O, 16.78.

EXAMPLE 10

Preparation of 7-(3-Methylamino-2-hydroxypropoxy) flavone hydrochloride

The free amine was prepared according to Method B from 7-(2,3-epoxypropoxy) flavone and 40% aqueous methylamine in 30% yield after column purification, m.p. 133°–4° (MeOH-$CH_2Cl_2$). The hydrochloride salt, m.p. 251°–52° (MeOH); yield 68% (purified).

Anal. Calc'd. for $C_{19}H_{20}ClNO_4 \cdot \frac{1}{2}H_2O$: C, 61.54; H, 5.71; Cl, 9.56; N, 3.78; O, 19.42. Found: C, 61.47; H, 5.82; Cl, 9.88; N, 3.63; O, 19.92.

EXAMPLE 11

Preparation of 7-(3-Ethylamino-2-hydroxypropoxy) flavone hydrochloride

According to Method B, the title compound was synthesized from the reaction of 7-(2,3-epoxypropoxy) flavone and 70% aqueous ethylamine followed by treatment with HCl/EtOH, as white prisms, m.p. 244°–46° (MeOH) in 36% yield. The free base was obtained after column purification as white crystals, m.p. 164°–65° (MeOH/ehter), yield 39%.

Anal. Calc'd. for $C_{20}H_{22}ClNO_4$: C, 63.91; H, 5.89; Cl, 9.43; N, 3.72; O, 17.02. Found: C, 64.07; H, 6.03; Cl, 9.65; N, 3.76; O, 17.14.

EXAMPLE 12

Preparation of 7-(3-n-butylamino-2-hydroxypropoxy) flavone hydrochloride

Using Method B, the reaction of 7-(2,3-epoxypropoxy) flavone and n-butylamine afforded the hydrochloride in 35% yield (purified) as white crystals, m.p. 224°–25° (MeOH). The free base was purified by high pressure liquid chromatography as an off-white powder, m.p. 143°–44° (53% yield).

Anal. Cal'd. for $C_{22}H_{26}ClNO_4$: C, 65.42; H, 6.48; Cl, 8.77; N, 3.46; O, 15.84. Found: C, 65.01; H, 6.83; Cl, 9.08; N, 3.33; O, 15.41.

EXAMPLE 13

Preparation of 7-(3-cyclohexylamino-2-hydroxypropoxy) flavone hydrochloride

The title compound was prepared according to Method B in 63% yield as a white powder, m.p. 242°–43° (MeOH). Its free base was purified by high pressure liquid chromatography and obtained as white powder, m.p. 174°–76° (63% yield).

Anal. Calc'd. for $C_{24}H_{28}ClNO_4 \cdot \frac{1}{2}H_2O$: C, 65.67; H, 6.66; N, 3,19; O, 16.40. Found: C, 65.34; H, 6.87; N, 3.16; O, 16.86.

EXAMPLE 14

Preparation of 7-(3-cyclopropylamino-2-hydroxypropoxy)-2,3-diphenylchromone

The amine was prepared according to Method B from cyclopropylamine and 7-(2,3-epoxypropoxy)-2,3-diphenylchromone and purified by high pressure liquid chromatography to give white crystals, m.p. 135°–137° (MeOH-ether), in 25% yield.

EXAMPLE 15

Preparation of 7-(3-amino-2-hydroxypropoxy) flavone hydrochloride 7-(2,3-Epoxypropoxy)flavone (13.3 g, 0.045 mol) in a presurre bottle was treated with a methanolic solution (90 ml) containing 1.87 g of ammonia (0.11 mol). The bottle was sealed and the suspension was heated at 50° for 12 hrs. A tlc (15% MeOH/$CHCl_3$) indicated that the starting material was gone, and the reaction mixture was cooled and filtered. The solid (5.32 g) thus obtained was shown by tlc to be a byproduct, m.p. 209°–12°. The filtrate, upon evaporation, afforded 7.0 g of a yellow solid, m.p. 121°–27°, which was purified by high pressure liquid chromatography to give 1.85 g of yellow powder, m.p. 154°–56°. (13% yield). The hydrochloride salt was prepared and recrystallized from MeOH, m.p. 191°–2°.

EXAMPLE 16

Preparation of 7-(3-propylamino-2-hydroxypropoxy)-3-benzylflavone hydrochloride

3-Benzyl-7-(2,3-epoxypropoxy)flavone

Using Method A, 3-benzyl-7-hydroxyflavone was converted to its corresponding epoxide, m.p. 133°–138°.

7-(2-hydroxy-3-propylaminopropoxy)-3-benzylflavone hydrochloride

The amine salt was prepared from 3-benzyl-7-(2,3-epoxypropoxy)flavone as described in Method B as white prisms, m.p. 196°–8° (iPrOH); yield, 50% (from the epoxide).

Anal. Cal'd. for $C_{28}H_{30}ClNO_4$: C, 70.07; H, 6.30; Cl, 7.39; N, 2.92. Found: C, 69.78; H, 6.32; Cl, 7.49; N, 2.74.

EXAMPLE 17

Preparation of 7-(2-hydroxy-3-isopropylaminopropoxy)chrysin hydrochloride

5-Hydroxy-7-(2,3-epoxypropoxy)flavone

Using Method A, the epoxide was prepared as a light yellow solid from chrysin hydrochloride in 26% yield (purified); m.p. 169°–170°.

Anal. Calc'd. for $C_{18}H_{13}O_5$: C, 69.89; H, 4.23; O, 25.86. Found: C, 69,47; H, 4.72; O, 26.04.

7-(2-hydroxy-3-isopropylaminopropoxy)chrysin hydrochloride

The hydrochloride was prepared as usual from the above epoxide and isopropylamine as a light yellow powder; m.p. 236°–37°. (dec. iPrOH); 45% yield.

Anal. Calc'd. for $C_{21}H_{24}CLNO_5$: C, 62.14; H, 5.96; Cl, 8.73; N, 3.45. Found: C, 61.90; H, 5.84; Cl, 8.72; N, 3.33.

EXAMPLE 18

Preparation of 7-(2-hydroxy-3-isopropylaminopropoxy)-2-methylisoflavone hydrochloride 7-(2,3-epoxypropoxy)-2-methylisoflavone Using Method A, the epoxide was synthesized from 7-hydro-2-methylisoflavone as white prisms.

7-(2-hydroxy-3-isopropylaminopropoxy)-2-methylisoflavone hydrochloride

The title compound was prepared as described in Method B from the above epoxide and isopropylamine as white prisms; m.p. 183°–5° (iProOH), in 40% yield.

Anal. Calc'd. for $C_{22}H_{26}ClNO_4$: C, 65.42; H, 6.49; N, 3.47; Cl, 8.78. Found: C, 65.25; H, 6.74; N, 3.39; Cl, 8.67.

EXAMPLE 19

Preparation of 7-(3-N-methyl-N-isopropylamino-2-hydroxypropoxy)-2-methylisoflavone methiodide 7-(2-hydroxy-3-isopropylaminopropoxy)-2-methylisoflavone (8.1 g, 0.021 moles) was added to a small amount of dry ether. The etheral solution under nitrogen was allowed to react with methyl iodide (9.0 ml) and stirred overnight. The solid formed was collected and washed with anhydrous ether. It was recrystallized twice from ethanol (abs.) to give 6.8 g (62% yield) of light yellow powder; m.p. 211°–213° C.

Anal. Calc'd. for $C_{24}H_{30}NO_4I$: C, 55.07; H, 5.77, I, 24.24; N, 2.67. Found: C, 54.89; H, 5.80; I, 24.06; N, 2.49.

EXAMPLE 20

Preparation of 7-(2-hydroxy-3-isopropylaminopropoxy)-2-trifluoromethylisoflavone hydrochloride 7-(2,3-epoxypropoxy)-2-trifluoromethylisoflavone The epoxide was prepared from 7-hydroxy-2-trifuoromethylisoflavone following Method A: m.p. 146°–148° ($CH_2Cl_2$); yield, 61%.

7-(2-hydroxy-3-isopropylaminopropoxy)-2-trifluoromethylisoflavone hydrochloride

Reaction of the corresponding epoxide with isopropylamine, as shown in Method B, afforded the title compound as white prisms, m.p. 220°–222° C.

Anal. Calc'd. for $C_{22}H_{23}ClFNO_4$: C, 57.71; H, 5.06; Cl, 7.74; F, 12.44; N, 3.05. Found: C, 57.88; H, 5.06; Cl, 7.52; F, 12.51; N, 2.97.

EXAMPLE 21

Preparation of 7-(2-hydroxy-3-isopropylaminopropoxy)-2-isopropylisoflavone maleate 7-(2,3-epoxypropoxy)-2-isopropylisoflavone The epoxide was prepared from 7-hydroxy-2-isopropylisoflavone by Method A; m.p. 139°–140° C. ($CH_2Cl_2$); yield, 27%.

7-(2-hydroxy-3-isopropylaminopropoxy)-2-isopropylisoflavone maleate

The corresponding epoxide was reacted with isopropylamine followed by maleic acid to give the matleate as white prisms in 94% yield, m.p. 187°–188°.

Anal. Calc'd. for $C_{28}H_{33}NO_8$: C, 65.74; H, 6.50; N, 2.73. Found: C, 65.77; H, 6.27;, N, 2.66.

EXAMPLE 22

Preparation of 7-(3-allylamino-2-hydroxypropoxy)-2,3-diphenylchromone

Using Method B, the reaction of 7-(2,3-epoxypropoxy)-2,3-diphenychromone and allylamine afforded the desired amine as white needles, m.p. 119°–120° (iPrOH); yield, 82%. Its hydrochloride salt had m.p. 140°–142° (iPrOH/phCH$_3$); containing water).

Anal. Calc'd. for $C_{27}H_{25}NO_4$ (the free base): C, 75.85; H, 5.89; N, 3.27; O, 14.97. Found: C, 75.87; H, 5.95; N, 3.14; O, 15.04.

EXAMPLE 23

Preparation of 7-(3-cyclopentylamino-2-hydroxypropoxy)-2,3-diphenylchromone hydrochloride Using Method B, the reaction of 7-(2,3-epoxypropoxy)-2,3-diphenylchromone and cyclopentylamine gave the title amine as white crystals; m.p. 162.5°–163° (iPrOH); yield 87%. Its hydrochloride salt was prepared as usual and melted at 155°–156° (iPrOH).

Anal. Calc'd. for $C_{29}H_{30}ClNO_4 \cdot 1\frac{1}{2}H_2O$: C, 67.11; H, 6.41; Cl, 6.83; N, 2.70; O, 16.95. Found: C, 67.04; H, 5.90; Cl, 6.70; N, 2.66; O, 17.04.

EXAMPLE 24

Preparation of 7-(3-sec-butylamino-2-hydroxypropoxy)-2,3-diphenylchromone

The title compound was synthesized according to Method B, in 98% yield, as white crystals, m.p. 139°–139.5°.

Anal. Calc'd. for $C_{28}H_{29}NO_4$: C, 75.82; H, 6.59; N, 3.15. Found: C, 75.50; H, 6.81; N, 3.10.

EXAMPLE 25

Preparation of 7-(3-N-methyl-N-propylamino-2-hydroxypropoxy)-2,3-diphenylchromone maleate Using Method B, the free base of the title compound was prepared from the corresponding epoxide and N-methylpropylamine. The obtained amine was dissolved in isopropyl alcohol and reacted with a solution of maleic acid in isoporpyl alcohol. The white crystals formed were collected; m.p. 135°–137°.

Anal. Calc'd. for $C_{32}H_{33}NO_8$: C, 68.68; H, 5.94; N, 2.50. Found: C, 68.88; H, 5.98; N, 2.26.

EXAMPLE 26

Preparation of 3-Methyl-7-(3-isopropylamino-2-hydroxypropoxy) flavone hydrochloride 3-Methyl-7-(2,3-epoxypropoxy)flavone Using Method A, 3-methyl-7-hydroxyflavone was converted to its corresponding 7-epoxypropyl ether, m.p. 231°–235° (crude); yield 86%.

3-Methyl-7-(2-hydroxy-3-isopropylaminopropoxy) flavone hydrochloride

The amine salt was prepared as described in Method B to give a white solid, m.p. 141°–144°.

Anal. Calc'd. for $C_{22}H_{26}ClNO_4$: C, 65.42; H, 6.48; Cl, 8.77; N, 3.46; O, 15.84. Found: C, 65.62; H, 6.61; Cl, 8.51; N, 3.33; O, 15.30.

Antihypertensive activity was determined in the spontaneously hypertensive rat. Animals were dosed with compound or control vehicle following a control blood pressure (systolic) and heart rate determination made by means of an inflatable tail cuff. Measurements were made over a 24 hour period. Five animals per test group were employed. A decrease in systolic blood pressure which was statistically different from both the control animals and the post dosage measurement is classified as minimal activity.

The following table gives minimal dosage required for minimal activity for the compounds of the Examples indicated and for a compound of the P. Da Re article, 3-methyl-7-(3-isopropylamino-2-hydroxypropoxy)flavone hydrochloride prepared using Method A and Method B, and shown in Example 26.

EXAMPLE 27

| Example No. | $R_1$ | $R_2$ | $R_3$ | $R_4$ | Activity mg./kg. |
|---|---|---|---|---|---|
| 1 | i-propyl | phenyl | phenyl | hydrogen | 8 |
| 2 | " | " | hydrogen | " | 17 |
| 3 | " | hydrogen | phenyl | " | 75 |
| 4 | n-propyl | phenyl | hydrogen | " | 12 |
| 5 | i-propyl | 2'Cl phenyl | " | " | 35 |
| 6 | " | phenyl | " | " | 75 |
| 7 | " | 4'Cl phenyl | " | " | 35 |
| 8 | n-propyl | phenyl | phenyl | " | 8 |
| 9 | cyclopropyl | " | hydrogen | " | 8 |
| 10 | methyl | " | " | " | 35 |
| 11 | ethyl | " | " | " | 35 |
| 12 | n-butyl | " | " | " | 17 |
| 13 | cyclohexyl | " | " | " | 17 |
| 14 | cyclopropyl | " | phenyl | " | 8 |
| 15 | hydrogen | " | hydrogen | " | 75 |
| 16 | n-propyl | " | benzyl | " | 75 |
| 17 | i-propyl | " | hydrogen | hydroxyl | 75 |
| 18 | " | methyl | phenyl | hydrogen | 35 |
| 19** | isopropyl | " | phenyl | hydrogen | 75 |
| 20 | i-propyl | $CF_3$ | " | " | 35 |
| 21 | " | i-propyl | " | " | 35 |
| 22 | allyl | phenyl | " | " | 75 |
| 23 | cyclopentyl | " | " | " | 75 |
| 24 | sec-butyl | " | " | " | 75 |
| 25 | n-propyl | " | " | " | 75 |
| 26 | i-propyl | " | methyl | " | 75 |

*R is hydrogen except in Examples 19 and 25 where it is methyl
**the quaternary methiodide.

These compounds do not exhibit beta-blocking activity when determined as antagonism of isoproterenol-induced beta stimulation of isolated rat heart or inhibition of isoproterenol-induced effects on the cardiovascular system of the anesthetized rat.

What is claimed is:

1. A method of reducing hypertension in an animal which comprises administering to the animal an amount effective to reduce hypertension of a chromone having the formula:

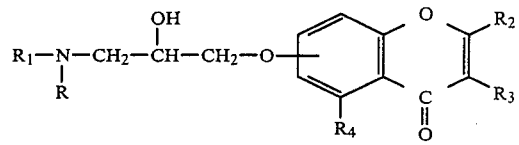

or a pharmaceutically acceptable or quaternary ammonium salt thereof wherein the side chain is in the 6 or 7 position of the chromone nucleus; R is H or methyl, $R_1$ is H, primary or secondary alkyl of 1 to 4 carbons; lower alkenyl or cycloalkyl of 3 to 6 carbons; $R_2$ is hydrogen, lower alkyl, $CF_3$, phenyl, o-halophenyl or p-halophenyl, $R_3$ is hydrogen or phenyl or benzyl and $R_4$ is hydrogen or hydroxyl; provided, however, that at least one of $R_2$ or $R_3$ is phenyl or substituted phenyl.

2. The method of claim 1, wherein said group is in the 7 position.

3. The method of claim 1, wherein $R_1$ is i-propyl, n-propyl or cyclopropyl, $R_2$ is phenyl, $R_3$ is phenyl or hydrogen and $R_4$ and R are hydrogen; provided, however, that $R_1$ is cyclopropyl or n-propyl when $R_3$ is hydrogen.

4. The method of claim 3 wherein $R_1$ is n-propyl.

5. The method of claim 3 wherein $R_3$ is phenyl.

6. The method of claim 3 wherein the amount of said chromone is at least sufficient to effect a 10% decrease in systolic blood pressure within 24 hours after administering said amount.

7. The method of claim 6 wherein said amount ranges from 0.1 mg. to 150 mg. per day, administered perorally.

8. The method of claim 7 wherein said amount ranges from 0.1 mg. to 50 mg. per day, administered perorally.

9. The method of claim 6 wherein said amount ranges from 0.1 mg. to 40 mg. per day administered parenterally.

10. The method of claim 6, wherein said amount ranges from 0.1 mg. to 10 mg. per day, adminstered parenterally.

* * * * *